(12) United States Patent
Thommen-Stamenkov et al.

(10) Patent No.: US 9,291,603 B2
(45) Date of Patent: Mar. 22, 2016

(54) INSPECTION VEHICLE FOR THE INSPECTION OF SUBSTANTIALLY CYLINDRICAL OBJECTS

(75) Inventors: Igor Thommen-Stamenkov, Olten (CH); Wolfgang Zesch, Windisch (CH); Stephane Laborde, Yerres (FR)

(73) Assignee: ALSTOM Technology Ltd, Baden (CH)

(*) Notice: Subject to any disclaimer, the term of this patent is extended or adjusted under 35 U.S.C. 154(b) by 7 days.

(21) Appl. No.: 13/228,482

(22) Filed: Sep. 9, 2011

(65) Prior Publication Data
US 2012/0060611 A1  Mar. 15, 2012

(30) Foreign Application Priority Data
Sep. 9, 2010 (CH) .................................... 1450/10

(51) Int. Cl.
*G01N 29/265* (2006.01)
*F01D 21/00* (2006.01)
*G01N 29/06* (2006.01)
*G01N 29/26* (2006.01)
(Continued)

(52) U.S. Cl.
CPC ............ *G01N 29/265* (2013.01); *F01D 21/003* (2013.01); *G01N 29/069* (2013.01); *G01N 29/262* (2013.01); *F01D 25/00* (2013.01); *F01D 25/285* (2013.01); *F05D 2260/80* (2013.01); *G01N 2291/2693* (2013.01)

(58) Field of Classification Search
CPC .............. G01N 29/069; G01N 2291/2693; G01N 29/265; G01N 29/26; G01N 29/225; F01D 21/003; F01D 25/285; F05D 2260/80

USPC ........................................................ 73/865.8
See application file for complete search history.

(56) References Cited

U.S. PATENT DOCUMENTS

| 5,619,423 A | * | 4/1997 | Scrantz ............. | G01N 29/2412 324/220 |
| 5,623,107 A | * | 4/1997 | Patterson, Sr. ..... | G01N 29/0645 73/865.8 |
| 6,016,701 A | * | 1/2000 | McClelland ......... | G01N 29/041 73/620 |

(Continued)

FOREIGN PATENT DOCUMENTS

| CN | 1973181 A | 5/2007 |
| JP | 61-114357 | 7/1986 |

(Continued)

OTHER PUBLICATIONS

European Patent Office, Search Report in Swiss Patent Application No. 01450/10 (Oct. 13, 2010).

(Continued)

*Primary Examiner* — Peter Macchiarolo
*Assistant Examiner* — Nathaniel Kolb

(57) ABSTRACT

An inspection vehicle for inspecting a substantially cylindrical object composed of a magnetizable material includes a chassis. A plurality of wheels is disposed on the chassis so as to be rotatable and is configured to move the chassis in a circumferential direction along an external surface of the cylindrical object, at least some of the plurality of wheels being motor-drivable. The plurality of wheels is disposed so as to provide a chassis clearance allowing a movement of the chassis over an obstruction on the external surface of the cylindrical object. A magnetic device is disposed on the chassis and is configured to hold the vehicle on the external surface of the cylindrical object.

22 Claims, 4 Drawing Sheets

(51) Int. Cl.
*F01D 25/00* (2006.01)
*F01D 25/28* (2006.01)

(56) References Cited

U.S. PATENT DOCUMENTS

| | | | | |
|---|---|---|---|---|
| 6,857,330 | B2* | 2/2005 | Murphy | F01D 25/285 73/865.8 |
| 6,886,422 | B2* | 5/2005 | King | G01B 5/205 73/116.03 |
| 2002/0104693 | A1* | 8/2002 | Moore | B62D 57/024 180/9.1 |
| 2003/0221497 | A1* | 12/2003 | Murphy | F01D 25/285 73/865.9 |
| 2008/0308324 | A1* | 12/2008 | Moser et al. | 180/6.7 |
| 2011/0169938 | A1* | 7/2011 | Webster | F22B 37/002 348/82 |
| 2011/0174565 | A1* | 7/2011 | Rochat | B62D 57/024 180/167 |
| 2012/0000290 | A1* | 1/2012 | Boone et al. | 73/660 |
| 2013/0061664 | A1* | 3/2013 | Boone | G01M 13/00 73/112.01 |

FOREIGN PATENT DOCUMENTS

| | | |
|---|---|---|
| JP | H6-160358 | 6/1994 |
| JP | H9-113675 | 5/1997 |
| JP | S63-30756 | 2/1998 |
| JP | 2000221178 A | 8/2000 |
| JP | 2009-128122 | 6/2009 |

OTHER PUBLICATIONS

Office action issued from Japanese Patent Office dated Jul. 7, 2014 for JP Application No. 2011-195676.

Office action issued from Chinese Patent Office dated Feb. 4, 2015 for CN Application No. 201110278755.4.

* cited by examiner

INSPECTION VEHICLE FOR THE INSPECTION OF SUBSTANTIALLY CYLINDRICAL OBJECTS

CROSS REFERENCE TO PRIOR APPLICATIONS

Priority is claimed to Swiss Patent Application No. CH 01450/10, filed on Sep. 9, 2010, the entire disclosure of which is hereby incorporated by reference herein.

FIELD

The present invention relates to the field of inspection of large parts of rotating machines.

BACKGROUND

Components which rotate at high speed, in particular rotors of steam turbines, or else other turbines, must be subjected from time to time to an inspection in which, in particular, the rotor of the turbine is examined for cracks. Cracks such as these often occur in circumferential blade slots, in which the blades of the turbine are held against the centrifugal forces that occur. Inspections such as these are frequently carried out using ultrasound sensors which are in the form of single-channel or multi-channel ultrasound measurement heads (phased arrays) and carry out delay-time duration determinations (so-called UT/PA/TOFD technology). During the inspections, one or two ultrasound sensors must be moved with great accuracy along the feet of the blades which are mounted in the rotor, in order to scan the critical area of the rotor, specifically the circumferential slots.

In order to allow good reproducibility of the results and a good quality of the determined data to be achieved during these inspections, the inspection should be linked to an appropriate position determination. Motorized inspection is a major advantage, on the one hand, because of the reproducible speed of travel, which can be maintained accurately, and, associated with this, the better reproducibility of the measurement results, and on the other hand because of the poor accessibility to the regions to be inspected (between the blade rows).

Since, during inspections such as these in the slots between the blade rows, the annular sealing strips which are present there in the slot base are often not removed in advance, they represent a serious obstruction to automated inspection.

Until now, it has been normal practice to carry out such inspections manually or with the sealing strips being removed before the inspection, and with the sealing strips being reinserted after the inspection. However, a process such as this is time-consuming, provides only a restricted data quality and results which cannot be reproduced well, while being impeded by a lack of accessibility.

A stationary robot arm has also already been used. In its application, the robot arm is highly flexible, but is dependent on having a large robot and requires a long setting-up time. However, it is particularly disadvantageous that the rotor to be inspected must be rotated, necessitating a (heavy and expensive) rotation mechanism.

Mobile scanners can move over the circumference of the rotor and carry out the required inspection in the process. These mobile scanners are generally equipped with broad magnetic wheels, which means that they cannot cope with obstructions which occur on the circumference of the rotor, in particular with annular sealing strips, a number of which may be present, and some of which may be separated by only 9 mm.

SUMMARY

In an embodiment, the invention provides an inspection vehicle for inspecting a substantially cylindrical object composed of a magnetizable material including a chassis. A plurality of wheels is disposed on the chassis so as to be rotatable and is configured to move the chassis in a circumferential direction along an external surface of the cylindrical object, at least some of the plurality of wheels being motor-drivable. The plurality of wheels is disposed so as to provide a chassis clearance allowing a movement of the chassis over an obstruction on the external surface of the cylindrical object. A magnetic device is disposed on the chassis and is configured to hold the vehicle on the external surface of the cylindrical object.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
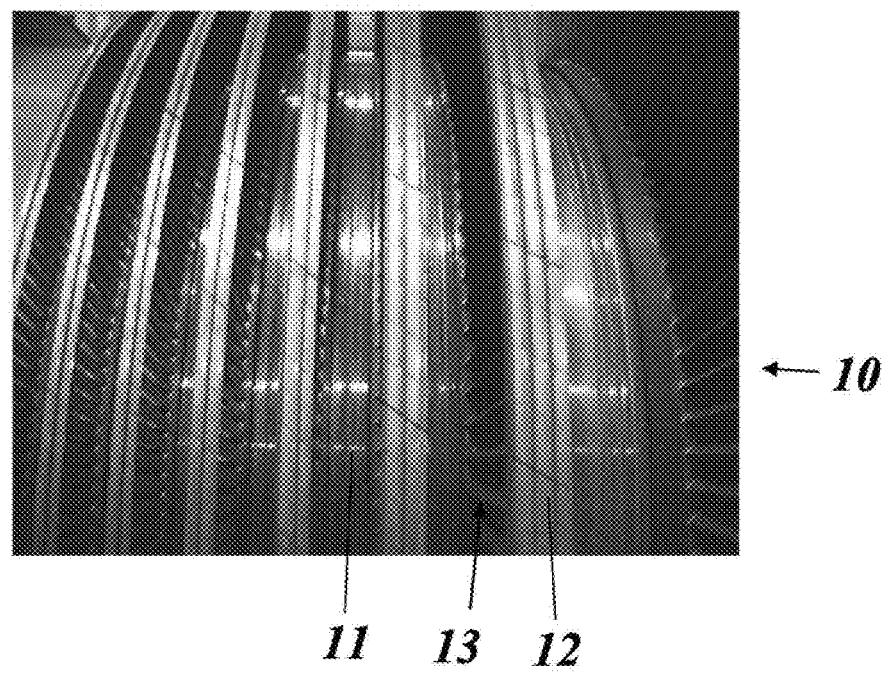
FIG. 1 shows a side view of a rotor of a steam turbine with the associated blade system.

An aspect of the invention is to provide an inspection vehicle which is suitable for automatic inspection of rotors, in which there are obstructions on the circumference, in particular in the form of annular sealing strips, which make it difficult for the vehicle to move over the circumference.

In an embodiment, the inspection vehicle according to the invention, which has a chassis and a plurality of wheels which are arranged on the chassis such that they can rotate and at least some of which can be driven by a motor or motors, such that the chassis can be moved on the wheels along the external circumference of the cylindrical object to be inspected, wherein magnetic means are arranged on the chassis and hold the inspection vehicle on the surface of the cylindrical object, is distinguished in that the inspection vehicle has adequate chassis clearance which allows it to move without any problems over obstructions which are located on the external circumference of the cylindrical object to be inspected, in particular one or more annular obstructions which project radially from the cylinder surface and the majority of which extend in the circumferential direction, in particular radially projecting sealing strips.

In an embodiment of the inspection vehicle according to the invention, the magnetic means comprise a magnet arrangement which is arranged under the chassis, in the area of the chassis clearance. The separation of wheels and magnetic means allows movement and adhesion of the vehicle to be optimized separately. In particular, the wheels can be chosen to be very narrow, thus also allowing the vehicle to be used between closely adjacent obstructions and sealing strips.

In another embodiment of the invention, the magnet arrangement comprises one or more permanent magnets. This allows high adhesion forces to be achieved without energy consumption.

In another embodiment of the invention, the magnet arrangement comprises one or more electromagnets, which can preferably be switched on and off. Although this means that energy must be consumed for adhesion, the adhesion can, however, be controlled for this purpose.

In another embodiment of the invention, in order to avoid obstructions, the distance between the magnet arrangement and the surface beneath, and/or the position of the magnet arrangement transversely with respect to the direction of travel, are/is adjustable. This allows the vehicle to be flexibly matched to different operating conditions.

In another embodiment of the invention, the magnet arrangement is provided with a non-magnetic cover in order to reduce the interaction with obstructions being moved over. This makes it possible to reduce, or completely avoid, damage in the event of collisions with the obstructions, and to prevent adhesion to a magnetic obstruction.

In another embodiment of the invention, the wheels can be adjusted transversely with respect to the direction of travel. This measure also leads to increased flexibility in use, since the track width can be adjusted for the type of obstruction.

In another embodiment of the invention, the wheels are themselves magnetic and form the magnetic means. In this case, there is no separate magnet arrangement, leading to an increased tolerance with respect to obstructions.

In another embodiment of the invention, the inspection vehicle has a drive unit which drives at least one of the wheels in a controllable manner. This allows automated, autonomous operation of the vehicle.

In another embodiment of the invention, means for lateral guidance of the vehicle are provided on the inspection vehicle.

In an embodiment, a guide structure which extends in the direction of travel is arranged as the lateral guide means on at least one longitudinal side of the vehicle, by means of which guide structure the inspection vehicle can be guided at a diameter step on the cylindrical object in the circumferential direction. However, it is also feasible to guide the vehicle on the circumferential sealing strips.

The guide structure preferably comprises an elongated guide rail.

If the guide structure or guide rail is magnetic, it is attracted by the guide contour. This allows guidance on both sides by only one rail.

In another embodiment of the invention, the guide means have sensors for measurement of the lateral clearance, which interact with means for controlling the direction of travel of the vehicle. A monitoring unit can then be used to regulate the lateral clearance on the basis of a predetermined value, which is constant or varies over time. In this case, by way of example, the vehicle can be actively controlled by means of an additional steering axle.

In another embodiment of the invention, the inspection vehicle has one or more sensors which are suitable for, preferably non-destructive, inspection of the cylindrical object. The sensors allow the object to be scanned over a wide range using the vehicle, and to be examined for changes.

In another embodiment of the invention, the sensors are attached adjustably and/or in a sprung manner to the end of a sensor arm, which extends from the chassis of the inspection vehicle in the direction of travel. The sensor head can thus be matched to the geometry of the object, and is at the same time less influenced by the vehicle itself.

In another embodiment of the invention is characterized in that the sensors are in the form of ultrasound sensors (UT sensors), in particular phased array sensors. This allows a multiplicity of inspections to be carried out using a proven technology, depending on the type of sensors. In this case, phased array sensors can cover a relatively large area of the object to be examined, by electronic scanning.

In another embodiment of the invention, movement sensors are provided on the inspection vehicle and record the distance traveled and/or the instantaneous speed of travel of the inspection vehicle. The movement sensors not only allow the movement of the vehicle to be monitored and controlled, but also allow the inspection data to be associated with the respective vehicle positions in order in this way to ensure that faults detected are localized reliably in the object.

In another embodiment of the invention, an encoder which records the rotation of at least one of the wheels is provided as the movement sensor. This allows the position and speed of the vehicle to be determined and monitored in a particularly simple manner.

In another embodiment of the invention, an external movement sensor is also provided, and records the movement of the vehicle relative to the surface beneath. The external movement sensor makes it possible to neutralize skidding of the wheels on the surface beneath.

In another embodiment of the invention, a control system is provided in order to control the movement of the inspection vehicle on the surface of the cylindrical object, which control system relates the inspection results to the respective position of the inspection vehicle on the surface of the cylindrical object.

FIG. 1 shows a photograph of a rotor 10 of a steam turbine which has a plurality of blade rows 12 with rotor blades 13 which are arranged around a central rotor shaft 11. The blade feet of the rotor blades 13 are held in annular circumferential blade slots and, between them, form a circumferential blade intermediate space 14, a detail of one of which is illustrated in the form of a cross section in FIG. 2. The blade intermediate space 14 in FIG. 2 comprises a rotor blade 13, which is seated in a circumferential blade slot in the rotor shaft 11, and is bounded at the side by the rotor blades 13, which can be used as lateral reference surfaces by a vehicle when moving away from the blade intermediate space 14.

Figure 2:
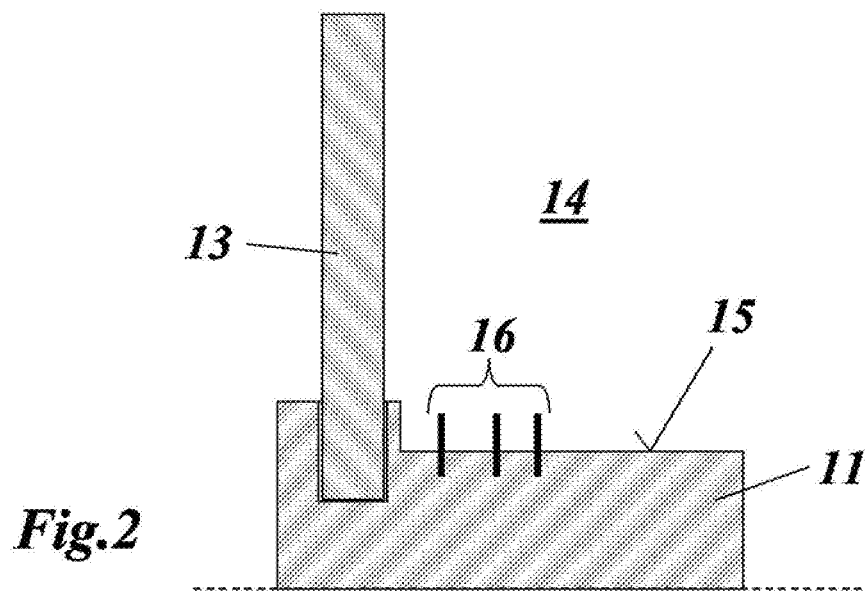
FIG. 2 shows the longitudinal section through a turbine rotor in the area of a diameter step or a slot, with a plurality of annular sealing strips being arranged in the slot base as obstructions for an inspection vehicle.

By way of example, FIG. 2 shows three sealing strips 16 in the outer surface 15 of the rotor shaft 11, which sealing strips 16 are located alongside one another and are introduced into the outer surface 15, but project radially somewhat beyond the outer surface 15. It is this type of obstruction, in particular, which makes it impossible to use a conventional vehicle.

Figure 3:
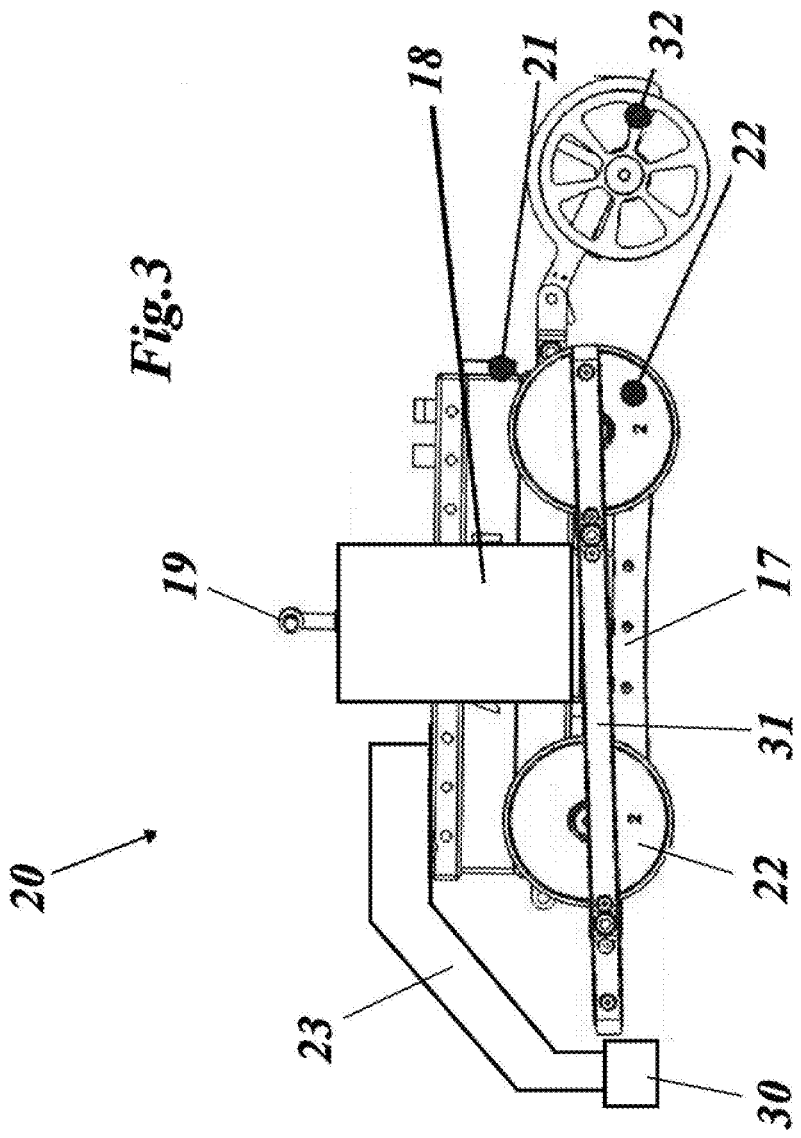
FIG. 3 shows the side view of an inspection vehicle according to one exemplary embodiment of the invention.
Figure 4:
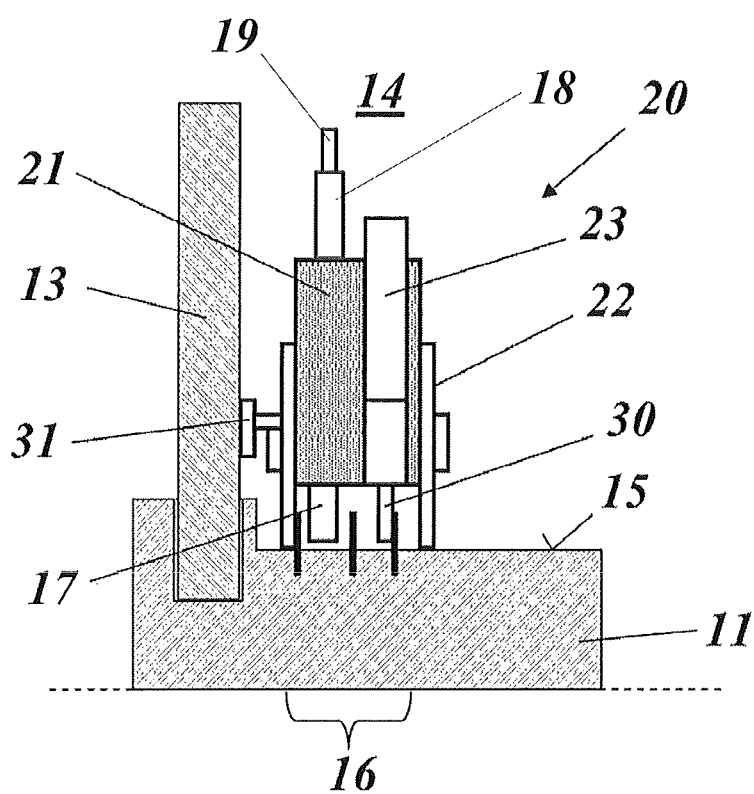
FIG. 4 shows the inspection vehicle as shown in FIG. 3, seen in the circumferential direction, during use on the slot base of a slot as shown in FIG. 2.

The novel inspection vehicle, in a proven exemplary embodiment which is illustrated in FIGS. 3 and 4, is designed such that its continued movement is not adversely affected by such obstructions. FIG. 3 shows the example of an inspection vehicle 20 according to the invention viewed from the side, while FIG. 4 shows the same vehicle viewed from the front.

The inspection vehicle 20 has a substantially rectangular compact chassis 21 to which a pair of wheels 22 are in each case fitted at the front and rear in the direction of travel, such that they can rotate, at least one pair of which wheels can be driven by a drive unit (42 in FIG. 5) which is accommodated in the chassis 21. As can be seen in the view from the front in FIG. 4, the wheels 22 are very narrow, in order to allow them to roll without any difficulties between closely adjacent sealing strips 16 on the outer surface 15. Furthermore, the wheels 22 have a comparatively large external diameter in order to provide the inspection vehicle 20 with the necessary chassis clearance in order to allow the vehicle to move safely over the sealing strips 16 which project from the outer surface 15 (FIG. 4).

A magnet arrangement 17 is arranged on the underside of the chassis 21 and has permanent magnets, which arrangement ensures that the inspection vehicle 20 is held securely on the circumferential surface of the rotor 10 during movement. The magnet arrangement 17 is designed to be slightly curved in order that it is better matched to the curved circumferential surface of the rotor. The magnet arrangement 17 is held on the underside of the chassis 21 by a magnet support 18, which is attached to the chassis 21 and whose height can be adjusted by means of an adjusting apparatus 19. It is thus possible to in each case manually adjust the height of the magnet arrangement 17 above the surface beneath, thus making it possible to move safely over obstructions, while at the same time applying the necessary adhesion forces for the vehicle. Furthermore, this makes it possible to reduce the magnetic adhesion force in a simple manner when placing the vehicle on the test object, and when removing the vehicle from it. The magnet support 18 with the magnet arrangement 17 fitted to it can, however, also preferably be moved transversely with respect to the direction of travel in order to allow the narrow magnet arrangement 17 to be adjusted to match a gap between adjacent sealing strips 16 (FIG. 4).

A sensor arm 23 is also fitted to the chassis 21, which sensor arm 23 extends in the direction of travel, projects well beyond the chassis 21 and is fitted with one (or more) appropriate sensor or sensors 30 at its front free end. This embodiment allows the inspection vehicle 20 to be flexibly matched to different situations on the rotor 10. As can be seen clearly in FIG. 4, this allows the inspection vehicle 20 to be moved in the blade intermediate space 14 of the rotor 10 without any difficulties, even though it is necessary to move over a plurality of sealing strips 16 as obstructions.

A guide rail 31 which extends in the direction of travel is arranged outside the wheels 22, at the side of the inspection vehicle 20, and allows the direction of travel of the inspection vehicle 20 to be aligned with a time reference surface, and to be parallel thereto.

A separate position measurement apparatus 32 is attached to the chassis 21 at the opposite end of the vehicle to the sensor head 28, and is seated on the bottom. The position measurement apparatus 32 allows the distance traveled by the inspection vehicle 20 to be recorded, and/or the speed of the inspection vehicle 20 to be determined, independently of any skidding of the wheels 22.

Figure 5:
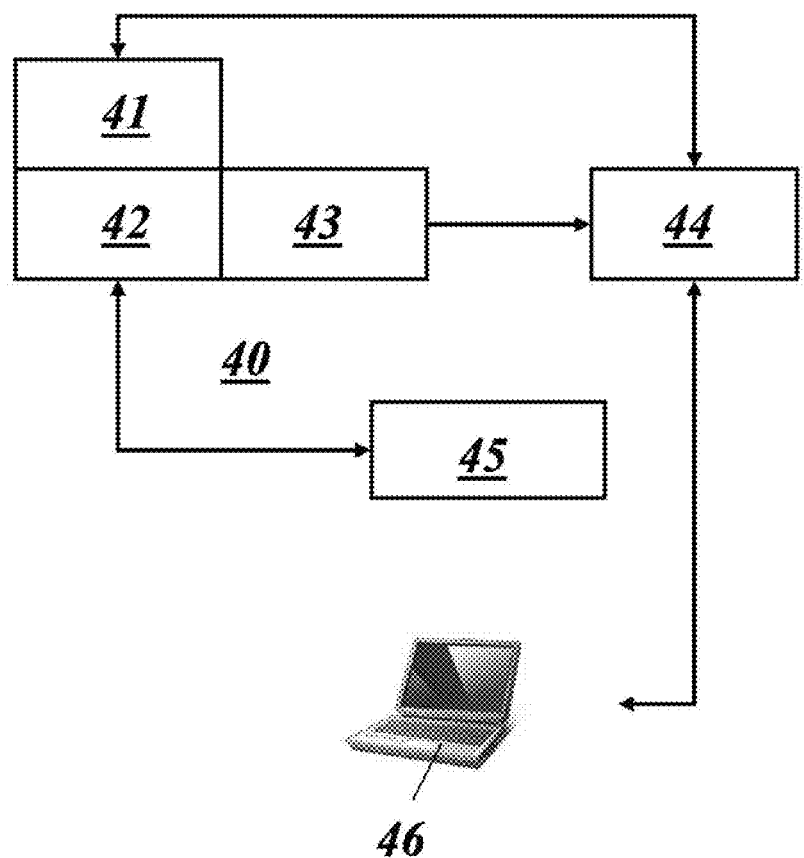
FIG. 5 shows the highly simplified schematic diagram of a control circuit for an inspection vehicle according to the invention.

The control circuit which is required for automatic inspection is illustrated schematically in FIG. 5. The drive 42 of the inspection vehicle 20 is connected to a power supply unit 45. A position measurement apparatus 43 produces position signals for scan software 44. Results from the sensors 41 are also fed into this software, for crack testing. The scan software 44, which runs on a computer 46, links the position and inspection data, and evaluates this data.

Overall, the proposed inspection vehicle results in the following advantages:
- the inspection is more reliable;
- no preparations, or only minor preparations, need be carried out for the inspection;
- the rotor need not be rotated for inspection, as a result of which there are no conflicts with other servicing tasks and there is no need for any heavy aids, which are often not available, for rotation of the rotor;
- the inspection is carried out very quickly;
- the inspection vehicle is small and light, and the associated equipment is easily transportable.

While the invention has been described with reference to particular embodiments thereof, it will be understood by those having ordinary skill the art that various changes may be made therein without departing from the scope and spirit of the invention. Further, the present invention is not limited to the embodiments described herein; reference should be had to the appended claims.

LIST OF REFERENCE SYMBOLS

10 Rotor (e.g. steam turbine)
11 Rotor shaft
12 Blade row
13 Rotor blade
14 Blade intermediate space (circumferential)
15 Outer surface (rotor shaft)
16 Sealing strip
17 Magnet arrangement
18 Magnet support
19 Adjusting apparatus
20 Inspection vehicle
21 Chassis
22 Wheel
23 Sensor arm
30 Sensor (for example ultrasound)
31 Guide rail (lateral)
32 Position measurement apparatus (external)
34 Arm
40 Control circuit
41 Sensors
42 Drive
43 Encoder (position measurement apparatus)
44 Scan software
45 Power supply unit
46 Computer

What is claimed is:

1. An inspection vehicle for inspecting a substantially cylindrical object composed of a magnetizable material, the vehicle comprising:
   a chassis;
   a plurality of wheels disposed on the chassis so as to be rotatable and configured to move the chassis in a circumferential direction along an external surface of the cylindrical object, at least one pair of the plurality of wheels being motor-drivable, the plurality of wheels disposed so as to provide a chassis clearance allowing a movement of the chassis over a plurality of obstructions projecting from the external surface of the cylindrical object, and at least one of the plurality of wheels dimensioned for rolling movement between two adjacent obstructions of the plurality of obstructions projecting from the external surface of the cylindrical object;
   a magnet arrangement to hold the vehicle to the external surface of the cylindrical object disposed underneath the chassis in the region of the chassis clearance between at least a pair of wheels among the plurality of wheels, the magnetic arrangement having a curvature-shaped profile to match a curvature of the external surface of the cylindrical object and dimensioned for extension between two adjacent obstructions of the plurality of obstructions projecting from the external surface of the cylindrical object; and
   a sensor arm having a first end arranged at the chassis, and a second end opposite the first end, the second end of the sensor arm having at least one sensor arranged thereon, the sensor arm extending from the first end at the chassis in a direction of travel of the vehicle to align the sensor parallel to the magnetic arrangement and adjacent to the external surface of the cylindrical object, and with the chassis clearance between the pair of wheels, to enable the at least one sensor to perform non-destructive inspection between two adjacent obstructions of the plurality of obstructions projecting from the external surface of the cylindrical object.

2. The inspection vehicle as recited in claim 1, wherein the cylindrical object is the rotor of a turbine, and wherein the plurality of obstructions includes an annular obstruction.

3. The inspection vehicle as recited in claim 2, wherein the annular obstruction includes a sealing strip projecting radially from the external surface of the turbine and extending in the circumferential direction.

4. The inspection vehicle as recited in claim 1, wherein the magnet arrangement includes at least one permanent magnet.

5. The inspection vehicle as recited in claim 1, wherein the magnet arrangement includes at least one electromagnet which can be activated and deactivated.

6. The inspection vehicle as recited in claim 1, wherein at least one of a position of the magnet arrangement transverse to the direction of travel of the vehicle, and a distance between the magnet arrangement and the external surface beneath the magnet arrangement, is adjustable to avoid any one of the plurality of obstructions.

7. The inspection vehicle as recited in claim 1, wherein the magnet arrangement includes a non-magnetic cover to reduce collision with any one of the plurality of obstructions.

8. The inspection vehicle as recited in claim 1, wherein the plurality of wheels is transversely adjustable with respect to an axial direction of the cylindrical object.

9. The inspection vehicle as recited in claim 1, further comprising a drive unit configured to drive at least one of the plurality of wheels to rotate.

10. The inspection vehicle as recited in claim 1, further comprising a lateral guidance device.

11. The inspection vehicle as recited in claim 10, wherein the lateral guidance device includes a guide structure extending in the direction of travel disposed on at least one longitudinal side of the vehicle and configured to guide the vehicle at a diameter step on the cylindrical object in a circumferential direction.

12. The inspection vehicle as recited in claim 11, wherein the guide structure includes an elongated guide rail.

13. The inspection vehicle as recited in claim 11, wherein the guide structure is magnetic.

14. The inspection vehicle as recited in claim 10, wherein the lateral guidance device interacts with a controller controlling a direction of travel of the vehicle.

15. The inspection vehicle as recited in claim 1, wherein the at least one sensor is attached to an end of the sensor arm in at least one of an adjustable manner, and a sprung manner.

16. The inspection vehicle as recited in claim 1, wherein the at least one sensor includes an ultrasound sensor.

17. The inspection vehicle as recited in claim 16, wherein the ultrasound sensor is a phased array sensor.

18. The inspection vehicle as recited in claim 1, further comprising at least one movement sensor disposed on the vehicle and configured to record at least one of a distance traveled, and an instantaneous speed of travel of the vehicle.

19. The inspection vehicle as recited in claim 18, wherein the at least one movement sensor includes an encoder configured to record a rotation of at least one of the plurality of wheels.

20. The inspection vehicle as recited in claim 19, further comprising an external movement sensor configured to record a movement of the vehicle relative to the external surface beneath the vehicle.

21. The inspection vehicle as recited in claim 1, further comprising a control system configured to control a movement of the vehicle on the external surface and configured to relate an inspection result to a respective position of the vehicle on the external surface.

22. The inspection vehicle recited in claim 1, wherein the sensor is laterally adjustable.

* * * * *

UNITED STATES PATENT AND TRADEMARK OFFICE
CERTIFICATE OF CORRECTION

PATENT NO. : 9,291,603 B2
APPLICATION NO. : 13/228482
DATED : March 22, 2016
INVENTOR(S) : Thommen-Stamenkov et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 9 days.

Signed and Sealed this
Twenty-sixth Day of July, 2016

Michelle K. Lee
*Director of the United States Patent and Trademark Office*